(12) United States Patent
Park

(10) Patent No.: US 7,416,845 B2
(45) Date of Patent: Aug. 26, 2008

(54) PH DEPENDENT ION EXCHANGE MATERIAL, SOLID SUBSTRATE HAVING THE MATERIAL IMMOBILIZED ON ITS SURFACE, AND METHOD OF ISOLATING A NUCLEIC ACID USING THE MATERIAL OR THE SOLID SUBSTRATE

(75) Inventor: Jong-myeong Park, Seoul (KR)

(73) Assignee: Samsung Electronics Co., Ltd. (KR)

( * ) Notice: Subject to any disclaimer, the term of this patent is extended or adjusted under 35 U.S.C. 154(b) by 203 days.

(21) Appl. No.: 11/430,358

(22) Filed: May 9, 2006

(65) Prior Publication Data

US 2006/0263812 A1    Nov. 23, 2006

(30) Foreign Application Priority Data

May 21, 2005    (KR) ............... 10-2005-0042782

(51) Int. Cl.
 C08Q 1/68    (2006.01)
 B01J 41/14    (2006.01)
 C08G 63/91    (2006.01)
 C12M 1/34    (2006.01)
(52) U.S. Cl. .......... 435/6; 435/287.2; 521/32; 525/54.2; 518/722; 526/25.4
(58) Field of Classification Search ......... 536/25.4, 536/25.41, 18.5; 518/722; 435/6, 287.1; 521/32; 525/54.2
 See application file for complete search history.

(56) References Cited

U.S. PATENT DOCUMENTS

| | | | | |
|---|---|---|---|---|
| 6,310,199 | B1 * | 10/2001 | Smith et al. | 536/25.4 |
| 6,806,362 | B2 * | 10/2004 | Smith et al. | 536/25.4 |
| 2001/0018513 | A1 | 8/2001 | Baker | |

* cited by examiner

Primary Examiner—Randy Gulakowski
Assistant Examiner—Michael M Bernshteyn
(74) Attorney, Agent, or Firm—Cantor Colburn LLP

(57) ABSTRACT

Provided are a pH dependent ion exchange material having a carboxyl group, an amino group, and a polyethylene oxide moiety, which is used for isolating a nucleic acid, a solid substrate having the material immobilized on its surface, and a method of isolating a nucleic acid using the material or the solid substrate. The pH dependent ion exchange material has at least two monomers selected from the group consisting of M0, M1, M2, M3 and M4 represented by the following formulae, provided that the pH dependent ion exchange material has at least one monomer selected from the group consisting of M1 and M2 and at least one monomer selected from the group consisting of M3 and M4:

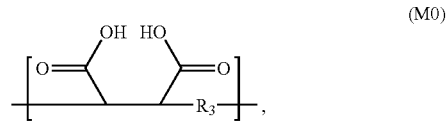

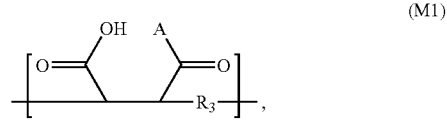

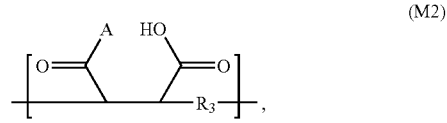

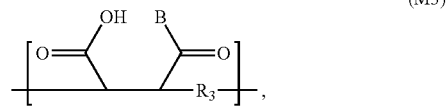

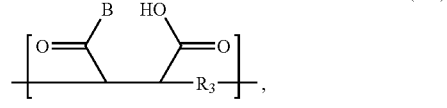

wherein
A is a base selected from the group consisting of —NH$(CH_2)_n$NH$_2$ and —NH$(CH_2)_n$Y, wherein n is an integer from 1 to 10 and Y is an aromatic base in which at least one of ring atoms is nitrogen,
B is —$(CH_2CHO)_n$OR$_2$, wherein n is 1-20 and R$_2$ is a C1-10 alkyl group or a protecting group, and
the pH dependent ion exchange material having a degree of polymerization of 2-30,000.

10 Claims, 1 Drawing Sheet

SEQUENCE LISTING

<160> NUMBER OF SEQ ID NOS: 1

<210> SEQ ID NO 1
<211> LENGTH: 50
<212> TYPE: DNA
<213> ORGANISM: Artificial Sequence
<220> FEATURE:
<223> OTHER INFORMATION: primer

<400> SEQUENCE: 1
ggcctcactt cctggggtca tgacccagg cctggaggcc tgcttccctt                50

PH DEPENDENT ION EXCHANGE MATERIAL, SOLID SUBSTRATE HAVING THE MATERIAL IMMOBILIZED ON ITS SURFACE, AND METHOD OF ISOLATING A NUCLEIC ACID USING THE MATERIAL OR THE SOLID SUBSTRATE

CROSS-REFERENCE TO RELATED PATENT APPLICATION

This application claims the benefit of Korean Patent Application No. 10-2005-0042782, filed on May 21, 2005, in the Korean Intellectual Property Office, the disclosure of which is incorporated herein in its entirety by reference.

BACKGROUND OF THE INVENTION

1. Field of the Invention

The present invention relates to a pH dependent ion exchange material having a carboxyl group, an amino group, and a polyethylene oxide moiety, a solid substrate having the material immobilized on its surface, and a method of isolating a nucleic acid using the material or the solid substrate.

2. Description of the Related Art pH dependent ion exchange matrices and methods of isolating nucleic acids using them are known. For example, U.S. published patent application No. 2001/0018513 describes a method of isolating a nucleic acid using a material containing an ionisable group which is positively charged at a first pH such that it can be bound to the nucleic acid and releasing the nucleic acid at a second pH which is higher than the first pH. Examples of the material containing an ionisable group include N-2-acetamido-2-aminoethanesulfonic acid (ACES), N-2-acetamido-2-imidodiacetic acid (ADA), N-trihydroxymethyl-methyl-2-aminoethanesulfonic acid (TES) and trihydroxymethylaminoethane (Tris), etc. U.S. Pat. No. 6,310,199 describes a method of isolating a nucleic acid using a pH dependent ion exchange matrix, the matrix comprising a silica magnetic particle and a plurality of first ion exchange ligands, each first ion exchange ligand comprising an aromatic hydrocarbon ring, a spacer covalently attached to the aromatic hydrocarbon ring, and a linker comprising a linker alkyl chain attached to the silica magnetic particle at its first end and attached to the spacer at its second end.

However, since the conventional pH dependent ion exchange materials have a high binding ability to proteins as well as to nucleic acids in a sample, the efficiency of selectively isolating the nucleic acids from the sample is low.

Thus, the inventors of the present invention searched for pH dependent ion exchange materials which can bind strongly to the nucleic acids at a first pH and release the nucleic acids at a second pH in a high ratio, but bind weakly to the proteins, and thus can be used for selectively isolating the nucleic acids from the sample, and discovered a pH dependent ion exchange material according the present invention.

SUMMARY OF THE INVENTION

The present invention provides a pH dependent ion exchange material which can bind strongly to nucleic acids at a first pH and release the nucleic acids at a second pH in a high ratio, but bind weakly to proteins.

The present invention also provides a solid substrate having the material immobilized on its surface.

The present invention also provides a method of isolating a nucleic acid using the material or the substrate having the material immobilized on its surface.

According to an aspect of the present invention, there is provided a pH dependent ion exchange material having a carboxyl group, an amino group, and a polyethylene oxide moiety, which is used for isolating a nucleic acid, the pH dependent ion exchange material having at least two monomers selected from the group consisting of M0, M1, M2, M3 and M4 represented by the following formulae, provided that the pH dependent ion exchange material has at least one monomer selected from the group consisting of M1 and M2 and at least one monomer selected from the group consisting of M3 and M4:

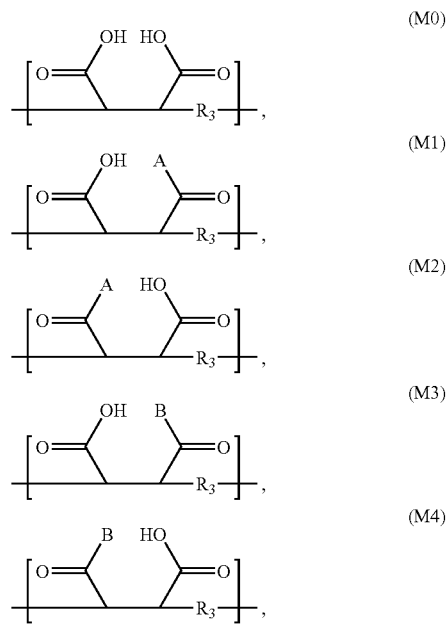

wherein

A is a base selected from the group consisting of —NH(CH$_2$)$_n$NH$_2$ and —NH(CH$_2$)$_n$Y, wherein n is an integer from 1 to 10 and Y is an aromatic base in which at least one of ring atoms is nitrogen, B is —(CH$_2$CHO)$_n$OR$_2$, wherein n is 1-20 and R$_2$ is a C1-10 alkyl group or a protecting group, and the pH dependent ion exchange material having a degree of polymerization of 2-30,000.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
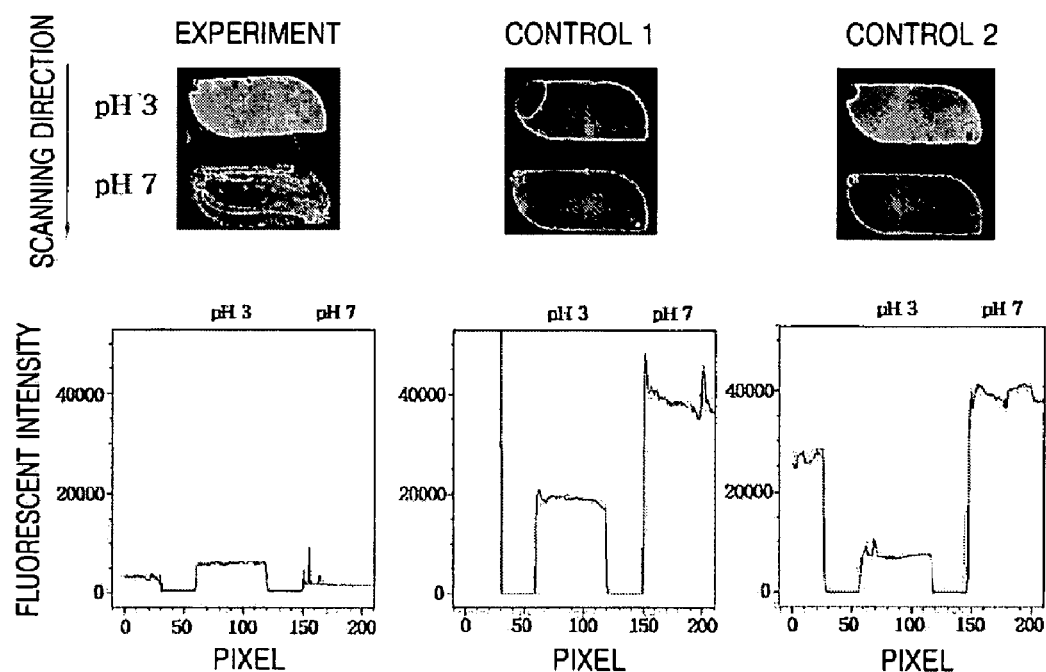
FIG. 1 illustrates photos of the substrates subjected to binding and elution of proteins at pH 3.0 and 7.0 and graphs showing their fluorescent intensities measured by scanning them on a flat plate.

According to an embodiment of the present invention, there is provided a pH dependent ion exchange material having a carboxyl group, an amino group, and a polyethylene oxide moiety, which is used for isolating a nucleic acid, the pH dependent ion exchange material having at least two monomers selected from the group consisting of M0, M1, M2, M3 and M4 represented by the following formulae, provided that the pH dependent ion exchange material has at least one monomer selected from the group consisting of M1 and M2 and at least one monomer selected from the group consisting of M3 and M4:

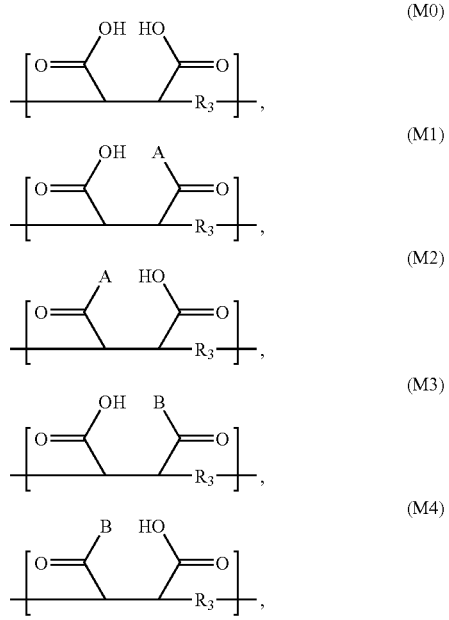

wherein

A is a base selected from the group consisting of —NH$(CH_2)_n$NH$_2$ and —NH$(CH_2)_n$Y, wherein n is an integer from 1 to 10 and Y is an aromatic base in which at least one of ring atoms is nitrogen, B is —$(CH_2CHO)_n OR_2$, wherein n is 1-20 and $R_2$ is a C1-10 alkyl group or a protecting group, and the pH dependent ion exchange material having a degree of polymerization of 2-30,000.

Examples of the pH dependent ion exchange material include those having a molar ratio of the carboxyl group in the ion exchange material to the amino group of A is 1.5-3.0:1.0.

Y in the formulae M1 and M2 may be a pyridinyl or imidazolyl group, but is not limited thereto.

Examples of the pH dependent ion exchange material also include those in which A is —NH$(CH_2)_2$NH$_2$, 4-(aminomethyl)pyridinyl, or 1-(3-aminopropyl)imidazolyl group.

Examples of the pH dependent ion exchange material also include those in which B is —$(CH_2CHO)_n OR_2$, wherein n is 1-5 and $R_2$ is selected from the group consisting of methyl, ethyl, propyl or butyl groups.

The pH dependent ion exchange material according to an embodiment of the present invention may be prepared using methods which are known in the art. For example, the material may be prepared by coupling a methylated polyethylene oxide ($CH_3O(CH_2CH_2O)_nH$) to polyanhydride (poly(ethylene-alt-maleic anhydride) (molecular weight=100,000-500,000)) under suitable conditions, and then coupling a base, such as ethylene diamine, 4-(aminomethyl)pyridine, or 1-(3-aminopropyl)imidazole, to the resultant product under suitable conditions. The above polyanhydride, methylated polyethylene oxide ($CH_3O(CH_2CH_2O)_nH$), ethylene diamine, 4-(aminomethyl)pyridine, and 1-(3-aminopropyl)imidazole may be easily synthesized by those having ordinary skill in the art or be commercially available.

According to another embodiment of the present invention, there is provided a solid substrate having the pH dependent ion exchange material immobilized on its surface.

The solid substrate having the material immobilized on its surface may have any form. For example, the solid substrate may have the form of plate, sphere, or microchannels, but is not limited thereto. Preferably, the solid substrate may have the form of microchannels in a microfluidic device.

A solid substrate on which the pH dependent ion exchange material to be immobilized may be selected from the group consisting of silica, fused silica, polyethylene, polypropylene, a slide glass, and a silicon wafer, but is not limited thereto.

The solid substrate according to an embodiment of the present invention may be prepared by activating an end portion of a chain of the pH dependent ion exchange material with an activating group, such as an aldehyde group and an ester group, and coupling the activated material to a solid substrate coated with an active group such as an amino group, but the preparation methods are not limited thereto. The activation of the ion exchange material and the solid substrate may be carried out using any methods which are known in the art. For example, the ion exchange material may be activated by oxidation of its end group or by introducing an active group by coupling the end group to an ester compound such as an acid anhydride. In addition, the solid substrate may be activated by coating an active material such as an amino group on a surface of the solid substrate, for example, using a spin coating method. In another method of immobilizing the ion exchange material on a surface of the solid substrate, the polyanhydride as describe above (for example, poly(ethylene-alt-maleic anhydride) (molecular weight=100,000-500,000)) is coated on an activated substrate and a polyethylene oxide having a protected end portion (for example, a methylated polyethylene oxide ($CH_3O(CH_2CH_2O)_nH$)) is coupled to the immobilized polyanhydride under suitable conditions, and then a base, such as ethylene diamine, 4-(aminomethyl)pyridine, or 1-(3-aminopropyl)imidazole, is coupled to the resultant product under suitable conditions. The above polyanhydride, polyethylene oxide having a protected end portion (for example, a methylated polyethylene oxide ($CH_3O(CH_2CH_2O)_nH$)), ethylene diamine, 4-(aminomethyl)pyridine, and 1-(3-aminopropyl)imidazole may be easily synthesized by those having ordinary skill in the art or be commercially available.

According to a still another embodiment of the present invention, there is provided a method of isolating a nucleic acid using the pH dependent ion exchange material having a carboxyl group, an amino group, and a polyethylene oxide moiety or the solid substrate having the material immobilized on its surface, comprising: contacting a sample containing the nucleic acid with the pH dependent ion exchange material or the solid substrate at a first pH; and exposing the ion exchange material having the nucleic acid bound thereto to a solution having a second pH which is higher than the first pH, to release the nucleic acid from the ion exchange material.

In the method according to an embodiment of the present invention, the first pH has a value at which the amino group of A in the material is positively charged and which is near a p$K_a$ value of the carboxyl group. Preferably, the first pH may be 2-4. The second pH has a value at which the carboxyl group (—COOH) in the material is negatively charged and which is near a $pK_a$ value of the amino group of A. Preferably, the second pH may be 5-10.

In the method according to an embodiment of the present invention, the contacting of the nucleic acid sample with the pH dependent ion exchange material or the solid substrate may be carried out in any solution which is known in the art (for example, PBS) and those having ordinary skill in the art may easily select the solution. The release of the nucleic acid from the ion exchange material or the solid substrate may be carried out in any solution which is known in the art (for example, a buffer such as PBS or water) and those having ordinary skill in the art may easily select the solution.

Hereinafter, the present invention will be described in more detail with reference to the following examples. However, these examples are given for the purpose of illustration and are not intended to limit the scope of the invention.

EXAMPLES

Comparative Example 1

Isolation of Nucleic Acid Using a Substrate Having a Polymer Containing a Carboxyl Group and an Amino Group Immobilized on its Surface In Comparative Example 1, a substrate having a pH dependent ion exchange material immobilized on its surface, the ion exchange material being composed of monomers M0, M1, and M2 having the following formulae was prepared. Then, DNAs were bound to the substrate at a first pH and the nucleic acids were recovered from the DNA-substrate complex at a second pH:

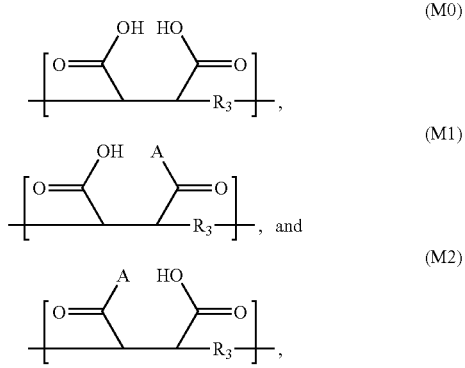

wherein

A is —NH(CH$_2$)$_2$NH$_2$, and

R$_3$ is —(CH$_2$)$_3$—.

The immobilization of the pH dependent ion exchange material composed of M0, M1, and M2 on the substrate was carried out as follows. First, a glass substrate coated with an amino group (Corning GAPS glass, Corning Corporation) was immersed in 200 mM (based on a repeat unit) polyanhydride (Poly(ethylene-alt-maleic anhydride)) (molecular weight (Mw)=100,000-500,000) in N-methyl-2-pyrrolidone (NMP) at room temperature for 1 hour, and then the substrate was washed with acetone and dried in a vacuum. The resultant glass substrate having polyanhydride bound thereto was immersed in ethylene diamine in NMP (a molar ratio of ethylene diamine:H$_2$O=4:6) in the presence of the catalyst triethylamine (TEA) at room temperature for 1 hour and then the substrate was washed with ethanol and dried. The concentration of ethylene diamine was 400 mM and the concentration of water was 600 mM.

DNAs having SEQ ID No. 1 labeled with Cy3 at a 5' end position were reacted with two glass substrates coated with the pH dependent ion exchange material composed of M0, M1, and M2 at pH 3. The reaction was performed by adding a 0.15 M sodium acetate solution containing 1 μM of the DNAs to a surface of each of the substrates, covering the substrate with a cover, and placing it at room temperature for 1 minute. After the reaction, the substrates were washed with 0.15 M sodium acetate at pH 7.0. Next, the fluorescent intensity was determined using Axon scanner (GenePix company, U.S.A.) at 532 nm (PMT 350). As a result, the fluorescent intensity at pH 3.0 was 21397 and the fluorescent intensity at pH 7.0 after the washing was 11135 (recovery 48%).

Further, IgG labeled with Alexa-532 was reacted with glass substrates coated with the pH dependent ion exchange material composed of M0, M1, and M2 at pH 3. The reaction was performed by adding a 0.15 M sodium acetate solution containing 1 μM of the IgG labeled with Alexa-532 to a surface of each of the substrates, covering the substrate with a cover, and placing it at room temperature for 1 minute. After the reaction, the fluorescent intensity was determined using Axon scanner (GenePix company, U.S.A.) at 532 nm (PMT 350). As a result, the fluorescent intensity at pH 3.0 was 39562.

From the above results, it was confirmed that when the pH dependent ion exchange material having the carboxyl group and amino group and not having a polyethylene oxide moiety is used, the recovery of the DNA is low and the ability of preventing the proteins from binding to the material is low.

Comparative Example 2

Isolation of Nucleic Acid Using a Substrate Having a Polymer Containing a Carboxyl Group and an Aromatic Amino Group on its Surface In Comparative Example 2, a substrate having a pH dependent ion exchange material immobilized on its surface, the ion exchange material being composed of monomers M0, M1, and M2 having the following formulae was prepared. Then, DNAs were bound to the substrate at a first pH and the nucleic acids were recovered from the DNA-substrate complex at a second pH:

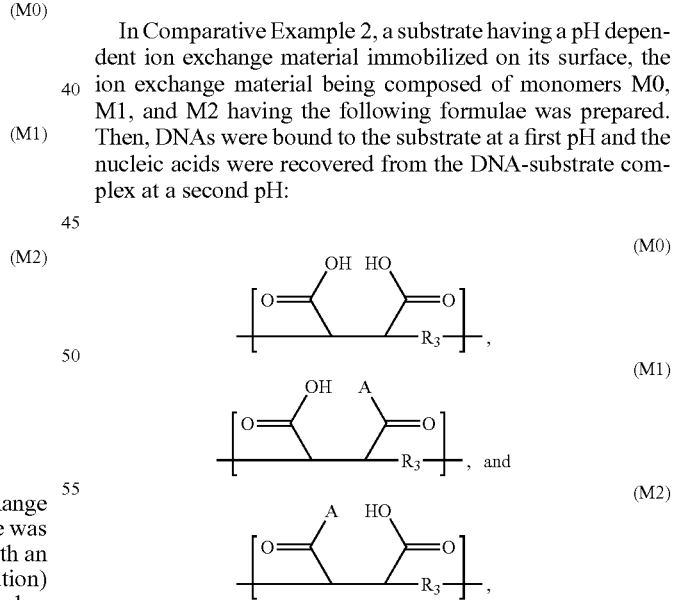

wherein

A is a 1-(3-aminopropyl)imidazolyl group, and

R$_3$ is —(CH$_2$)$_3$—.

The immobilization of the pH dependent ion exchange material composed of M0, M1, and M2 on the substrate was carried out as follows. First, a glass substrate coated with an amino group (Corning GAPS glass, Corning Corporation)

was immersed in 200 mM (based on a repeat unit) polyanhydride (Poly(ethylene-alt-maleic anhydride)) (molecular weight (Mw)=100,000-500,000) in N-methyl-2-pyrrolidone (NMP) at room temperature for 1 hour, and then the substrate was washed with acetone and dried in a vacuum. The resultant glass substrate having polyanhydride bound thereto was immersed in 1-(3-aminopropyl)imidazole in NMP (a molar ratio of 1-(3-aminopropyl)imidazole:$H_2O$=4:6) in the presence of the catalyst TEA at room temperature for 1 hour and then the substrate was washed with ethanol and dried. The concentration of 1-(3-aminopropyl)imidazole was 400 mM and the concentration of water was 600 mM.

DNAs having SEQ ID No. 1 labeled with Cy3 at a 5' end position were reacted with two glass substrates coated with the pH dependent ion exchange material composed of M0, M1, and M2 at pH 3. The reaction was performed by adding a 0.15 M sodium acetate solution containing 1 µM of the DNAs to a surface of each of the substrates, covering the substrate with a cover, and placing it at room temperature for 1 minute. After the reaction, the substrates were washed with 0.15 M sodium acetate at pH 7.0. Next, the fluorescent intensity was determined using Axon scanner (GenePix company, U.S.A.) at 532 nm (PMT 350). As a result, the fluorescent intensity at pH 3.0 was 18209 and the fluorescent intensity at pH 7.0 after the washing was 1519 (recovery 91%). It was confirmed that when an aromatic amino group is used, the recovery of nucleic acid is greatly increased.

Further, IgG labeled with Alexa-532 was reacted with glass substrates coated with the pH dependent ion exchange material composed of M0, M1, and M2 at pH 3. The reaction was performed by adding a 0.15 M sodium acetate solution containing 1 µM of the IgG labeled with Alexa-532 to a surface of each of the substrates, covering the substrate with a cover, and placing it at room temperature for 1 minute. After the reaction, the fluorescent intensity was determined using Axon scanner (GenePix company, U.S.A.) at 532 nm (PMT 350). The fluorescent intensity at pH 3.0 was 28608. Although the binding amount of protein was reduced by about 30% compared to the amount in Comparative Example 1 wherein the ion exchange material having ethylene diamine was used, the binding amount of protein was still large. Thus, there is still a need for a pH dependent ion exchange material which can reduce the binding amount of protein and increase the recovery of nucleic acids.

Example 1

Estimation of Resistance to Protein Binding of a pH Dependent Ion Exchange Material Having a Methylated Polyethylene Oxide In Example 1, a substrate having a pH dependent ion exchange material immobilized on its surface, the ion exchange material being composed of monomers M0, M3, and M4 having the following formulae was prepared. Then, DNAs were bound to the substrate at a first pH and the nucleic acids were recovered from the DNA-substrate complex at a second pH:

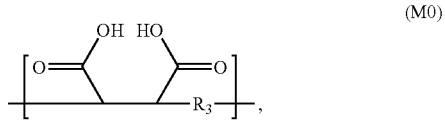
(M0)

-continued

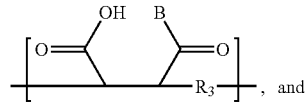
(M3)

, and

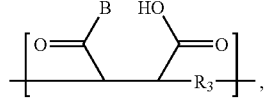
(M4)

, wherein
B is —O(CH$_2$CH$_2$O)$_3$OMe, and
R$_3$ is —(CH$_2$)$_3$—.

The immobilization of the pH dependent ion exchange material composed of M0, M3, and M4 on the substrate was carried out as follows. First, a glass substrate coated with an amino group (Corning GAPS glass, Corning Corporation) was immersed in 200 mM (based on a repeat unit) polyanhydride (Poly(ethylene-alt-maleic anhydride)) (molecular weight (Mw)=100,000-500,000) in NMP at room temperature for 1 hour, and then the substrate was washed with acetone and dried in a vacuum. The resultant glass substrate having polyanhydride bound thereto was immersed in tri(ethylene glycol)monomethyl ether in NMP (a molar ratio of tri(ethylene glycol)monomethyl ether:$H_2O$=4:6) in the presence of a catalyst TEA at room temperature for 1 hour and then the substrate was washed with ethanol and dried. The concentration of tri(ethylene glycol)monomethyl ether was 400 mM and the concentration of water was 600 mM.

IgG labeled with Alexa-532 was prepared by reacting human IgG (Sigma, U.S.A.) with Alexa 532 using Alexa Fluor 532 Monoclonal Labeling Kit (Molecular Probe). The IgG labeled with Alexa-532 was reacted with two glass substrates coated with the pH dependent ion exchange material composed of M0, M3, and M4 at pH 3 and 7. The reaction was performed by adding a 0.15 M sodium acetate solution containing 1 µM of the IgG labeled with Alexa-532 to a surface of each of the substrates, covering the substrate with a cover, and placing it at room temperature for 1 minute. After the reaction, the substrates were washed with a 0.15 M sodium acetate solution at pH 3 and 7, respectively, and then the fluorescent intensity was determined using Axon scanner (GenePix company, U.S.A.) at 532 nm (PMT 350). FIG. 1 illustrates photos of the substrates subjected to binding and elution of proteins at pH 3.0 and 7.0 and graphs showing their fluorescent intensities measured by scanning them on a flat plate; and As control groups, a glass substrate having an oxide film (SiO$_2$) (Control 1) and a glass substrate having a self-assembled monolayer (SAM) of tri(ethylene glycol)monomethyl ether (HO(CH$_2$CH$_2$O)$_3$Me) (Control 2) were subjected to the same procedures as described above. Control 2 was prepared as follows. First, tri(ethylene glycol)monomethyl ether (8.75 mmol) was stirred in the presence of NaH (17.5 mmol) at room temperature for 30 minutes, and 11-bromo-1-undecene (17.5 mmol) was added to the resultant solution to obtain CH$_2$=CH(CH$_2$)$_9$O(CH$_2$CH$_2$O)$_3$CH$_3$. The formation of this product was confirmed by 1H NMR showing the formation of double bond. Then, the resultant product CH$_2$=CH(CH$_2$)$_9$O(CH$_2$CH$_2$O)$_3$CH$_3$ and HSi(OMe)$_3$ were refluxed for about 3 hours in the presence of the catalyst $H_2PtCl_6$ to obtain $(OMe)_3Si(CH_2)_{11}O(CH_2CH_2O)_3Me$. The formation of this product was confirmed by 1H NMR showing the disappearance of the double bond. The resultant product $(OMe)_3Si(CH_2)_{11}O(CH_2CH_2O)_3Me$ was added to a glass substrate to obtain a glass substrate having the SAM of tri(ethylene glycol)monomethyl ether (Control 2).

Referring to FIG. 1, it was confirmed that the substrate having tri(ethylene glycol)monomethyl ether immobilized on its surface had a less binding amount of the proteins than the glass substrate having an oxide film ($SiO_2$) (Control 1) and the glass substrate having the SAM of tri(ethylene glycol) monomethyl ether (Control 2).

Example 2

Mechanism of Resistance to Protein Binding of a pH Dependent Ion Exchange Material Having a Methylated Polyethylene Oxide In Example 2, a substrate having a pH dependent ion exchange material immobilized on its surface, the ion exchange material being composed of monomers M0, M3, and M4 having the following formulae was prepared. Then, DNAs were bound to the substrate at a first pH and the nucleic acids were recovered from the DNA-substrate complex at a second pH:

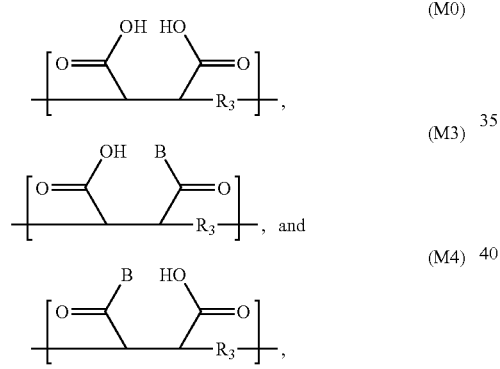

wherein
B is —$O(CH_2CH_2O)_3Me$, and
$R_3$ is —$(CH_2)_3$—.

The immobilization of the pH dependent ion exchange material composed of M0, M3, and M4 on the substrate was carried out as follows. First, a glass substrate coated with an amino group (Corning GAPS glass, Corning Corporation) was immersed in 200 mM (based on a repeat unit) polyanhydride (Poly(ethylene-alt-maleic anhydride)) (molecular weight (Mw)=100,000-500,000) in NMP at room temperature for 1 hour, and then the substrate was washed with acetone and dried in a vacuum. The resultant glass substrate having polyanhydride bound thereto was immersed in tri(ethylene glycol)monomethyl ether in NMP (a molar ratio of tri(ethylene glycol)monomethyl ether:$H_2O$=4:6) in the presence of the catalyst TEA at room temperature for 1 hour and then the substrate was washed with ethanol and dried. The concentration of tri(ethylene glycol)monomethyl ether was 400 mM and the concentration of water was 600 mM.

As control groups, a glass substrate having the polyanhydride bound thereto was immersed in ethylene diamine in NMP (a molar ratio of ethylene diamine:$H_2O$=4:6) (Control 1) or water (Control 2) for 1 hour at room temperature, and then washed with ethanol and dried. The concentration of ethylene diamine was 400 mM and the concentration of water was 600 mM.

Figure 2:
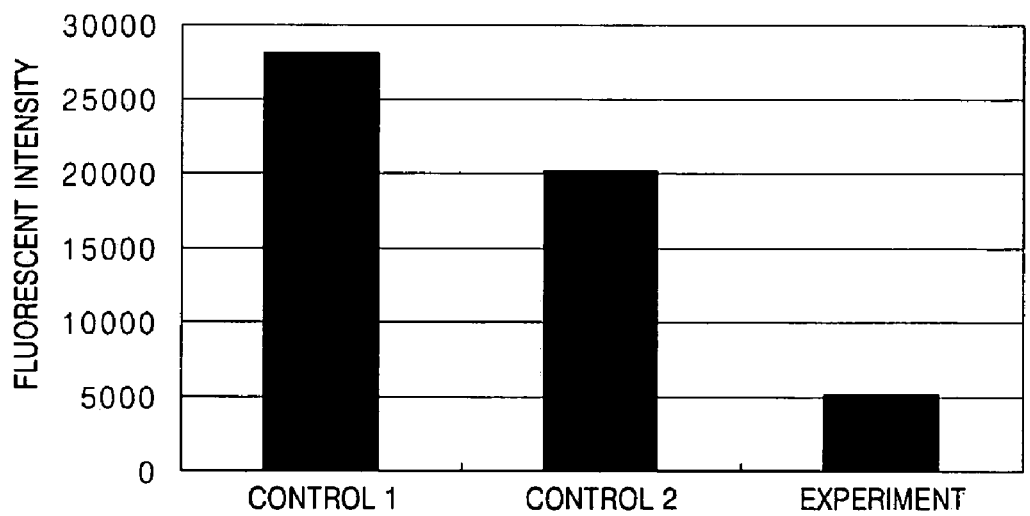
FIG. 2 illustrates a graph showing fluorescent intensities of the substrates subjected to binding and elution of proteins at pH 3, measured by scanning them on a flat plate.

IgG labeled with Alexa-532 was reacted with two glass substrates coated with the pH dependent ion exchange material composed of M0, M3, and M4 at pH 3 and 7. The reaction was performed by adding a 0.15 M sodium acetate solution containing 1 μM of the IgG labeled with Alexa-532 to a surface of each of the substrates, covering the substrate with a cover, and placing it at room temperature for 1 minute. After the reaction, the substrates were washed with a 0.15 M sodium acetate solution at pH 3 and 7, respectively, and then the fluorescent intensity was determined using Axon scanner (GenePix company, U.S.A.) at 532 nm (PMT 350). FIG. 2 illustrates a graph showing fluorescent intensities of the substrates subjected to binding and elution of proteins at pH 3, measured by scanning them on a flat plate.

Referring to FIG. 2, it was confirmed that the substrate having tri(ethylene glycol)monomethyl ether and the carboxyl group immobilized on its surface had a remarkably less binding amount of the protein than the glass substrate having the ethylene diamine and the carboxyl group (Control 1) and the glass substrate having only the carboxyl group (Control 2). It was confirmed from the results that the substrate having the tri(ethylene glycol)monomethyl ether and the carboxyl group prepared in Example 1 had the resistance to the protein binding due to the function of the tri(ethylene glycol)monomethyl ether, rather than due to the function of carboxyl group.

Example 3

Efficiencies of Binding and Eluting Nucleic Acid and Protein when Using a pH Dependent Ion Exchange Material Having a Carboxyl Group, an Amino Group, and a Methylated Polyethylene Oxide In Example 3, a substrate having a pH dependent ion exchange material having a carboxyl group, an amino group, and a polyethylene oxide moiety, which is used for isolating a nucleic acid, immobilized on its surface, was prepared. The ion exchange material having at least two monomers selected from the group consisting of M0, M1, M2, M3 and M4 represented by the following formulae, provided that the pH dependent ion exchange material has at least one monomer selected from the group consisting of M1 and M2 and at least one monomer selected from the group consisting of M3 and M4. Then, DNAs or proteins were bound to the substrate at a first pH and the DNA or proteins were recovered from the DNA- or protein-substrate complex at a second pH.

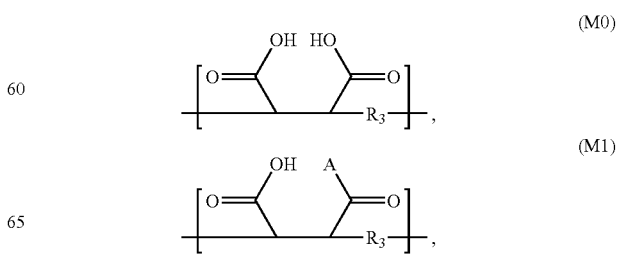

-continued

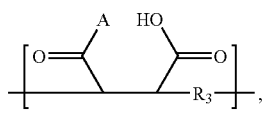

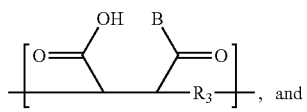, and

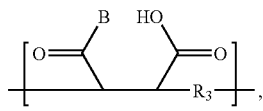

wherein

A is —NH(CH$_2$)$_2$NH$_2$ (Test 1) or -1-(3-aminopropyl)imidazolyl group (Test 2), B is —(CH$_2$CHO)$_3$OCH$_3$, and R$_3$ is —(CH$_2$)$_3$—.

The immobilization of the pH dependent ion exchange material composed of M0, M1, M2, M3 and M4 on the substrate was carried out as follows. First, a glass substrate coated with an amino group (Corning GAPS glass, Corning Corporation) was immersed in 200 mM (based on a repeat unit) polyanhydride (Poly(ethylene-alt-maleic anhydride)) (molecular weight (Mw)=100,000-500,000) in NMP at room temperature for 1 hour and then the substrate was washed with acetone and dried in a vacuum. The resultant glass substrate having polyanhydride bound thereto was immersed in tri(ethylene glycol)monomethyl ether in NMP (a molar ratio of tri(ethylene glycol)monomethyl ether:H$_2$O=4:6) in the presence of the catalyst TEA at room temperature for 1 hour and then the substrate was washed with ethanol and dried (Test 1 and Test 2). The concentration of tri(ethylene glycol) monomethyl ether was 20 mM and the concentration of water was 30 mM.

The glass substrate having the tri(ethylene glycol)monomethyl ether-coupled polyanhydride bound thereto was immersed in ethylene diamine in NMP (Control 1) (a molar ratio of ethylene diamine:H$_2$O=4:6) or 1-(3-aminopropyl) imidazole (Control 2) (a molar ratio of 1-(3-aminopropyl) imidazole:H$_2$O=4:6) in the presence of the catalyst TEA at room temperature for 1 hour and then the substrate was washed with ethanol and dried. The concentration of ethylene diamine or 1-(3-aminopropyl)imidazole was 2 mM and the concentration of water was 3 mM.

DNAs having SEQ ID No. 1 labeled with Cy3 at a 5' end position were reacted with two glass substrates coated with the pH dependent ion exchange material at pH 3. The reaction was performed by adding a 0.15 M sodium acetate solution containing 1 µM of the DNAs to a surface of each of the substrates, covering the substrate with a cover, and placing it at room temperature for 1 minute. After the reaction, the substrates were washed with 0.15 M sodium acetate at pH 7.0. Next, the fluorescent intensities were determined using Axon scanner (GenePix company, U.S.A.) at 532 nm (PMT 350). The fluorescent intensities measured at pH 3.0 and 7.0 are shown in Table 1.

TABLE 1

| (Fluorescent Intensity) | Control 1 | Control 2 | Test 1 | Test 2 |
|---|---|---|---|---|
| Binding | 44566 | 41066 | 38904 | 38640 |
| Elution | 14809 | 14608 | 6011 | 3939 |
| Recovery (%) | 66.8 | 64 | 85 | 90 |

Referring to Table 1, it was confirmed that the recovery of nucleic acid was greatly increased by using the pH dependent ion exchange material according to an embodiment of the present invention.

Further, IgG labeled with Alexa-532 was reacted with the glass substrates (Control 1, Test 1, and Test 2) at pH 3. The reaction was performed by adding a 0.15 M sodium acetate solution containing 1 µM of the IgG labeled with Alexa-532 to a surface of each of the substrates, covering the substrate with a cover, and placing it at room temperature for 1 minute. After the reaction, the fluorescent intensity was determined using Axon scanner (GenePix company, U.S.A.) at 532 nm (PMT 350). The fluorescent intensities of the proteins bound to the substrate at pH 3.0 are shown in Table 2.

TABLE 2

| (Fluorescent Intensity) | Control 1 | Test 1 | Test 2 |
|---|---|---|---|
| Binding (pH 3.0) | 7247 | 5572 | 3625 |
| Relative Ratio (%) | 100 | 76.9 | 50 |

Referring to Table 2, it was confirmed that the protein binding was greatly reduced by using the pH dependent ion exchange materials according to embodiments of the present invention.

It was confirmed from Example 3 that the recovery of nucleic acid can be increased and non-specific binding of protein can be remarkably reduced using the pH dependent ion exchange material according to embodiments of the present invention. Thus, the pH dependent ion exchange material according to embodiments of the present invention can be useful for isolating the nucleic acid.

By using the pH dependent ion exchange material or the substrate having the material immobilized on its surface according to the present invention, the efficiency of binding the nucleic acid to the ion exchange material at the first pH and the efficiency of recovering the nucleic acid from the ion exchange material at the second pH can be increased and the non-specific binding of protein to the ion exchange material can be remarkably reduced.

In the method of isolating the nucleic acid according to the present invention, the pH dependent ion exchange material having resistance to protein binding is used, and thus, the nucleic acid can be efficiently isolated from the ion exchange material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A pH dependent ion exchange material having a carboxyl group, an amino group, and a polyethylene oxide moiety, which is used for isolating a nucleic acid, the pH dependent ion exchange material having at least two monomers selected from the group consisting of M0, M1, M2, M3 and M4 represented by the following formulae, provided that the pH dependent ion exchange material has at least one monomer selected from the group consisting of M1 and M2 and at least one monomer selected from the group consisting of M3 and M4:

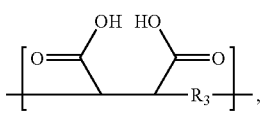 (M0)

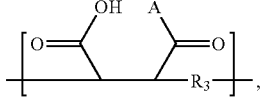 (M1)

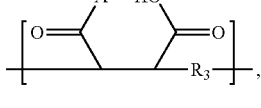 (M2)

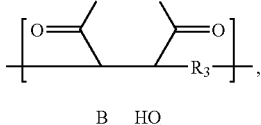 (M3)

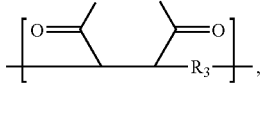 (M4)

wherein

A is a base selected from the group consisting of —NH(CH$_2$)$_n$NH$_2$ and —NH(CH$_2$)$_n$Y, wherein n is an integer from 1 to 10 and Y is an aromatic base in which at least one of ring atoms is nitrogen, B is —(CH$_2$CHO)$_n$OR$_2$, wherein n is 1-20 and R$_2$ is a C1-10 alkyl group or a protecting group, R$_3$ is —(CH$_2$)$_3$ and the pH dependent ion exchange material having a degree of polymerization of 2-30,000.

2. The pH dependent ion exchange material of claim 1, wherein a molar ratio of the carboxyl group in the ion exchange material to the amino group of A is 1.5-3.0:1.0.

3. The pH dependent ion exchange material of claim 1, wherein A is —NH(CH$_2$)$_2$NH$_2$, 4-(aminomethyl)pyridinyl, or 1-(3-aminopropyl)imidazolyl group.

4. A solid substrate having the pH dependent ion exchange material of claim 1 immobilized on its surface.

5. The solid substrate of claim 4, having the form of microchannels in a microfluidic device.

6. The solid substrate of claim 4, wherein a solid substrate on which the ion exchange material to be immobilized is selected from the group consisting of silica, fused silica, polyethylene, polypropylene, a slide glass, and a silicon wafer.

7. A method of isolating a nucleic acid using a pH dependent ion exchange material, comprising:
contacting a sample containing a nucleic acid with the ion exchange material of claim 1 at a first pH; and
exposing the pH dependent ion exchange material having the nucleic acid bound thereto to a solution having a second pH which is higher than the first pH, to release the nucleic acid from the pH dependent ion exchange material.

8. The method of claim 7, wherein the first pH is 2-4 and the second pH is 5-10.

9. A method of isolating a nucleic acid, comprising:
contacting a sample containing a nucleic acid with a solid substrate at a first pH, wherein the solid substrate has the pH dependent ion exchange material of claim 1 immobilized on its surface; and
exposing the solid substrate having the nucleic acid bound thereto to a solution having a second pH which is higher than the first pH, to release the nucleic acid from the pH dependent ion exchange material.

10. The method of claim 9, wherein the first pH is 2-4 and the second pH is 5-10.

* * * * *